United States Patent [19]

Bender

[11] 4,186,205

[45] Jan. 29, 1980

[54] 2,3-DI(4-SUBSTITUTED PHENYL)-6,7-DIHYDRO-5H-PYRROLO[1,2-A]IMIDAZOLES

[75] Inventor: Paul E. Bender, Cherry Hill, N.J.

[73] Assignee: SmithKline Corporation, Philadelphia, Pa.

[21] Appl. No.: 1,620

[22] Filed: Jan. 8, 1979

[51] Int. Cl.$^2$ .................. A61K 31/415; C07D 487/04
[52] U.S. Cl. ................................ 424/273 R; 548/324
[58] Field of Search ..................... 548/324; 424/273 R

[56] References Cited

U.S. PATENT DOCUMENTS

| | | | |
|---|---|---|---|
| 3,455,924 | 7/1969 | Lednicer | 260/307 R |
| 4,046,898 | 9/1977 | Shaw | 548/324 |

OTHER PUBLICATIONS

Hill et al., Chem. Abst. 1975, vol. 83, No. 130927g.
Kaye et al., J. Amer. Chem. Soc., 1953, vol. 75, pp. 746–748.
Kochergin, Chem. Abst. 1972, vol. 76, No. 25170n.
Okuda et al., J. Amer. Chem. Soc. 1959, vol. 81, pp. 740–743.
Shaw, Chem. Abst. 1976, vol. 85, No. 143109h, (Abstract Ger. Offen. No. 2,603,399).
Hill et al., J. Org. Chem., 1975, vol. 40, pp. 2562–2565.
Kochergin et al., Khim. Geterotskil Soeden 1971, vol. 7, pp. 826–830.

*Primary Examiner*—Natalie Trousof
*Attorney, Agent, or Firm*—Janice E. Williams; William H. Edgerton; Alan D. Lourie

[57] ABSTRACT

New 6,7-dihydro-5H-pyrrolo[1,2-a]imidazoles having substituted phenyl groups in the 2- and 3- positions are disclosed. These compounds regulate cell-mediated immunity and/or have anti-arthritic activity and are useful to relieve inflammation, for example in the treatment of rheumatoid arthritis.

12 Claims, No Drawings

2,3-DI(4-SUBSTITUTED PHENYL)-6,7-DIHYDRO-5H-PYRROLO[1,2-A]IMIDAZOLES

This invention relates to new 6,7-dihydro-5H-pyrrolo-[1,2-a]imidazoles having substituted phenyl groups in the 2- and 3-positions. These compounds regulate cell-mediated immunity and/or have anti-arthritic activity and are useful to relieve inflammation, for example in the treatment of rheumatoid arthritis.

The compounds of this invention are represented by the following structural formula:

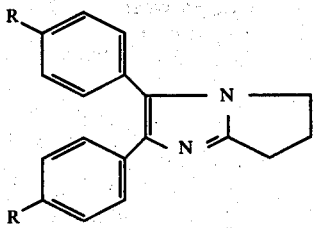

FORMULA I in which R is lower alkoxy of from one to four carbon atoms, methylthio or chloro, or a non-toxic, pharmaceutically acceptable salt thereof.

Two examples of 2,3-diphenyl substituted pyrrolo-[1,2-a]imidazoles are reported in the literature. Hill et al., *J. Org. Chem.*, 40(17):2562 (1975), describe the compound 2,3-diphenyl-6,7-dihydro-5H-pyrrolo[1,2-a]imidazole and Kochergin et al., *Khim. Geterotsikl Soedin* 7(6):826 (1971), report the compound 2,3,6-triphenyl-7H-pyrrolo-[1,2-a]imidazole. 6,7-Dihydro-5H-pyrrolo[1,2-a]imidazoles having a substituted aryl group in the 6-position and substituted with hydrogen or alkyl in the 2-, 3-, 5- and 7-positions are disclosed in German Offenlegungsschrift No. 2,603,399. In addition, 2,3-dianisylimidazo[1,2-z]pyridine is disclosed in U.S. Pat. No. 3,455,924; 2,3-diphenyl-5,6,7,8-tetrahydroimidazo[1,2-a]pyridine is described by Hill et al., supra; and Okuda et al. *J. Am. Chem. Soc.* 81:740 (1959) and Kaye et al., *J. Am. Chem. Soc.* 75:746 (1953) both report the compound 2,3-diphenylimidazo[1,2-a]pyridine. The compounds of Formula I are not believed to be known to the art.

The compounds of this invention are prepared by reaction of a 2-halo-1,2-di(substituted phenyl)ethanone with 2-amino-4,5-dihydro-3H-pyrrole as shown below:

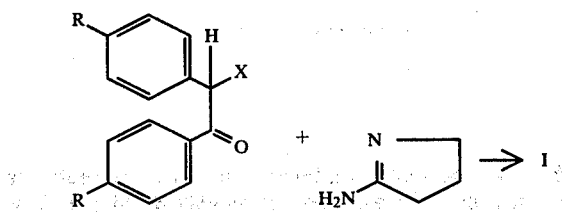

where R is as defined as above and X is halo, preferably chloro or bromo. The reaction is carried out at a temperature of from about 20° C. to about 45° C., preferably at ambient temperature, in a polar organic solvent such as N,N-dimethylformamide using an excess of the pyrrole, preferably about a 3:1 molar ratio of the starting materials. Isolation of the product employing standard techniques affords a compound of Formula I which may be converted to a salt by known procedures, for example by reaction with an acid.

The 2-halo-1,2-di(substituted phenyl)ethanone starting materials are either known to the art or are preferred by treatment of the corresponding bis (4,4'-substituded)benzoin with a reagent such as thionyl chloride.

Alternatively, the compounds of Formula I where R is lower alkoxy are prepared by reaction of 2,3-di(4hydroxyphenyl)-6,7-dihydro-5H-pyrrolo[1,2-a]imidazole or a salt thereof with sodium hydroxide followed by treatment with an alkyl halide such as ethyl iodide. The 2,3-di-(4-hydroxyphenyl)-6,7-dihydro-5H-pyrrolo[1,2-a]imidazole is obtained from reaction of 2-amino-4,5-dihydro-3H-pyrrole with an appropriately substituted ethanone compound where R is methanesulfonate and X is bromo followed by hydrolysis of the product thus formed in aqueous base or, preferably, by treatment of 2,3-di(4-methoxyphenyl)-6,7-dihydro-5H-pyrrolo[1,2-a]imidazole with boron tribromide according to known procedures. The methaneslfonate substituted bromoethanone compound is prepared by treatment of the corresponding ethanone where R is hydroxy and X is hydrogen with methanesulfonly chloride followed by bromination of the mesylated product, all according to known procedure.

The pharmaceutically acceptable acid addition salts of the compounds of Formula I are formed with strong of moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The compounds of this invention are useful as antiarthritic agents and as regulators of cell-mediated immunity.

The ability to regulate cell-mediated immunity is determined by the oxazolone-induced contact sensitivity test procedure in which changes in mouse paw edema produced by administration of the test compound are measured. This test procedure is described by Griswold et at., *Cellular Immunology* 11.198 (1974) and Griswold et al., *Inflammation* 2(4):277 (1977). The implication of cell-mediated immune reactivity in rheumatoid arthritis is described by Basch et al., *J. Rheumatology* 4:377 (1977). Some of the compounds of this invention enhance the oxazolone-induced response at doses of about 25 mg/kg, orally. Specific examples of this activity exhibited by certain compounds of this invention appear in Table 1.

TABLE 1

OXAZOLONE INDUCED CONTACT SENSITIVITY

| COMPOUND | Dose (mg/kg) (based on free base) | % Increase Over Controls of Mouse Paw Edema Volume |
|---|---|---|
| 2,3-Di(4-chlorophenyl)-6,7-dihydro-5H-pyrrolo[1,2-a]imidazole | 25 | 111 |
| 2,3-Di(4-methylthiophenyl)-6,7-dihydro-5H-pyrrolo[1,2-a]imidazole | 25 | 40 |
| 2,3-Di(4-isopropoxyphenyl)-6,7-dihydro-5H-pyrrolo[1,2-a]imidazole hydrochloride | 25 | 127 |

The anti-arthritic activity of the compounds of this invention is demonstrated by their ability to inhibit adjuvant induced polyarthritis in rats as measured by reduction of rat paw edema at daily doses of about 12.5–100 mg/kg orally. In this test procedure, adjuvant arthritis is produced in rats by a single intradermal injection of 0.75 mg. of *Mycobacterium butyricum* suspended in white paraffin oil into the left hindpaw footpad. The injected paw becomes inflamed (increased volume) and reaches maximum size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight and further increase in the volume of the injected left hind leg. Test compounds are administered daily beginning on the day of the adjuvant injection for seventeen days thereafter exclusive of days 4, 5, 11 and 12. Anti-inflammatory activity is shown by a decrease in volume of the inflamed leg and antiarthritic activity is shown by the ability to protect the animals against development of both primary and secondary lesions of adjuvant arthritis. Specific examples of this activity exhibited by certain compounds of this invention appear in Table 2.

TABLE 2

ADJUVANT INDUCED ARTHRITIS

| COMPOUND | Dose (mg/kg/day) (based on free base) | Injected (left) Hindleg Volume (cc.) Day 3 | Injected (left) Hindleg Volume (cc.) Day 16 | Uninjected (right) Hind-Leg Volume (cc.) Day 16 |
|---|---|---|---|---|
| 2,3-Di(4-methoxyphenyl)-6,7-dihydro-5H-pyrrolo[1,2-a]imidazole | 50 | −25 | −32 | −42 |
| 2,3-Di(4-chlorphenyl)-6,7-dihydro-5H-pyrrolo[1,2-a]imadazole | 50 | −19 | NS* | −19 |
| 2,3-Di(4-methylthiophenyl)-6,7-dihydro-5H-pyrrolo[1,2-a]imidazole | 50 | −26 | −30 | −30 |
| 2,3-Di(4-ethoxyphenyl)-6,7-dihydro-5H-pyrrolo[1,2-a]imidazole | 50 | −31 | −36 | −38 |
| Prednisolone | 20 | −35 | −43 | −58 |

*NS = not significant

Some of the compounds of this invention, namely 2,3-di(4-chlorophenyl)-6,7-dihydro-5H-pyrrolo[1,2-a]imidazole and 2,3-di(4-methylthiophenyl)-6,7-dihydro-5H-pyrrolo[1,2-a]imidazole, exhibit both regulation of cell-mediated immunity and anti-arthritic activity.

Because of the pharmacological profile of the compounds of this invention, it is expected that they would be useful as anti-inflammatory agents in man. Some of the compounds are also useful as anti-arthritic agents.

The compounds of this invention are administered in conventional dosage forms prepared by combining a compound of Formula I or a salt thereof in an amount sufficient to produce activity with a standard pharmaceutical carrier according to conventional procedures. These procedures may involve mixing, granulating and compressing or dissolving the ingredients as appropriate to the desired preparation. The resulting pharmaceutical compositions are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include a time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampule or a nonaqueous liquid suspension.

To obtain a stable water soluble dose form, a pharmaceutically acceptable acid addition salt, preferably hydrochloride or sulfate, of a compound of Formula I is dissolved in an aqueous solution of an organic or inorganic acid, such as a 0.3 M solution of succinic acid or, preferably, citric acid. In addition to sulfate and hydrochloride, methanesulfonate, phosphate and hydrobromide are exemplary of other water soluble salts.

Preferably, each dosage unit will contain the active ingredient in an amount of from about 25 mg to about 200 mg.

The method of regulating cell-mediated immunity and/or producing anti-arthritic activity by administering internally to an animal a compound of Formula I is also an object of this invention. The compound is administered in amounts sufficient to produce the activity desired. The route of administration may be orally or parenterally. The daily dosage regimen will be preferably from about 75 mg to about 600 mg. When the method is carried out as described above, the desired activity is produced.

One skilled in the art will recognize that in determining the amounts of the active ingredient in the claimed compositions and used in the claimed methods, the activity of the chemical ingredient as well as the size of the host animal must be considered.

The following examples do not limit the disclosure but are illustrative of the invention. All temperatures are in degrees Centigrade (°C) unless otherwise noted.

EXAMPLE 1

2,3-Di(4-methoxyphenyl)-6,7-dihydro-5H-pyrrolo[1,2-a]imidazole

To 300 ml of dry N,N-dimethylformamide was added 30. g (0.09 mol) of 2-bromo-1,2-di(4-methoxyphenyl)ethanone and 19.5 g (0.27 mol) of 2-amino-4,5-dihydro-3H-pyrrole. The mixture was stirred for three days at 25° with the exclusion of moisture. The reaction mixture was poured into water and the aqueous suspension was extracted three times with methylene chloride. The organic extracts were combined and washed six times with water, then dried ($K_2CO_3$). The solvent was evaporated and the residue was recrystallized from chloroform-hexane and dried overnight (80° in vacuo) to give the title compound, m.p. 146°–147.5°.

$C_{20}H_{20}N_2O_2$.

Calculated: 74.98% C; 6.29% H, 8.74% N; Found: 75.17% C; 6.52% H; 8.98% N.

A solution of 2,3-di(4-methoxyphenyl)-6,7-dihydro-5H-pyrrolo[1,2-a]imidazole in ethanol was treated with a slight excess of 48% hydrobromic acid diluted with ethanol. The solvent was removed in vacuo to give, after recrystallization from chloroform-hexane, the title compound as its hydrobromide salt.

$C_{20}H_{20}N_2O_2 \cdot HBr \cdot 0.75\ H_2O$:

Calculated: 57.91% C; 5.47% H; 6.75% N; Found: 57.97% C; 5.30% H; 6.50% N.

EXAMPLE 2

2,3-Di(4-ethoxyphenyl)-6,7-dihydro-5H-pyrrolo[1,2-a]imidazole

A solution of 46.5 g (0.19 mol) of boron tribromide in about 240 ml of dry methylene chloride was added dropwise with stirring over a 90 minute period to a solution of 35.0 g (0.11 mol) of 2,3-di(4-methoxyphenyl)-6,7-dihydro-5H-pyrrolo[1,2-a]imidazole in 600 ml of dry methylene chloride maintained at −75° under a nitrogen atmosphere. The solution was then decanted and the remaining solid material was slurried with methylene chloride and water, collected by filtration and dried to give 2,3-di-(4-hydroxyphenyl)-6,7-dihydro-5H-pyrrolo[1,2-a]imidazole hydrobromide.

2,3-Di(4-hydroxyphenyl)-6,7-dihydro-5H-pyrrolo[1,2-a]imidazole hydrobromide (7.0 g, 0.019 mol) was dissolved in 100 ml of dry N,N-dimethylformamide. Nitrogen was bubbled through the solution for 15 minutes, then 4.1 g (0.084 mol) of a 50% oil dispersion of sodium hydride was added. When gas evolution ceased, 6.1 g (0.039 mol) of ethyl iodide was added dropwise. The solution was stirred at 20° for one hour, then an additional 3.2 g (0.021 mol) of ethyl iodide was added. The reaction mixture was stirred another hour, then it was poured into ice/water. The aqueous suspension was thoroughly extracted with methylene chloride and the combined extracts were washed three times with water, dried ($K_2CO_3$) and concentrated. Hexane was added to the residue and the resulting solid material was chromatographed on an alumina dry column with methylene chloride as eluant. The resulting oily product was crystallized from methylene chloride-hexane and dried (70° in vacuo) to give the title compound, m.p. 135°–137.5°.

$C_{22}H_{24}N_2O_2$:

Calculated: 75.83% C; 6.94% H; 8.04% N; Found: 75.80% C; 6.96% H; 8.12% N.

EXAMPLE 3

2,3-Di(4-isopropoxyphenyl)-6,7-dihydro-5H-pyrrolo[1,2-a]-imidazole

Nitrogen was bubbled through a solution of 10.0 g (0.027 mol) of 2,3-di(4-hydroxyphenyl)-6,7-dihydro-5H-pyrrolo[1,2-a]imidazole hydrobromide in 25 ml of dry N,N-dimethylformamide, 5.8 g (0.12 mol) of a 50% oil dispersion of sodium hydride was added and the mixture was stirred under nitrogen until gas evolution ceased. To the suspension was added 9.6 g (0.056 mol) of isopropyl iodide. The mixture was heated with stirring at 95°–100° for 75 minutes, an additional 5.0 g (0.030 mol) of isopropyl iodide was added and the mixture was heated at 100° for three hours and then stirred at 25° overnight. The reaction mixture was then poured into ice/water. The solid was collected by filtration and washed once with water then three times with pentane. Successive chromatography of the material on silica gel eluting with 2% methanol in methylene chloride and on an alumina dry column eluting with methylene chloride-hexane (2:1) and then with methylene chloride alone gave the title compound as an oil.

The title compound was dissolved in ethyl ether and an ethereal hydrochloric acid solution was added to give 2,3-di(4-isopropoxyphenyl)-6,7-dihydro-5H-pyrrolo[1,2-a]imidazole hydrochloride, m.p. 259°–262° (dec.)

$C_{24}H_{28}N_2O_2 \cdot HCl$:

Calculated: 69.80% C; 7.08% H; 6.78% N; Found: 69.79% C; 7.18% H; 6.58% N.

EXAMPLE 4

2,3-Di(4-chlorophenyl)-6,7-dihydro-5H-pyrrolo[1,2-a]imidazole

A mixture of 6.2 g (0.018 mol) of 2-bromo-1,2-di-(4-chlorophenyl)ethanone and 4.6 g (0.054 mol) of 2-amino-4,5-dihydro-3H-pyrrole in 60 ml of dry N,N-dimethylformamide was stirred at 25° with exclusion of water for five days. The mixture was then poured into water and the aqueous solution was extracted three times with methylene chloride. The extracts were combined and washed eight times with water, dried ($K_2CO_3$) and evaporated. The residue was chromatographed on silica gel (dry column) with 1% tetrahydrofuran in chloroform and 5% tetrahydrofuran in chloroform as eluants. The product-containing section was washed with methanol to remove the product which was, after evaporation of the methanol, recrystallized from methanol-water to give the title compound, m.p. 189°–192°.

$C_{18}H_{14}N_2Cl_2 \cdot 0.25\ H_2O$:

Calculated: 64.78% C; 4.38% H; 8.39% N; Found: 64.92% C; 4.75% H; 8.40% N.

EXAMPLE 5

2,3-Di(4-methylthiophenyl)-6,7-dihydro-5H-pyrrolo[1,2-a]-imidazole

To a solution of 160 g (1.05 mol) of 4-methylthiobenzaldehyde in 320 ml of 95% ethanol was added a solution of 32 g (0.49 mol) of potassium cyanide in 320 ml of water. The mixture was refluxed for three hours, then allowed to cool to ambient temperature. The solid which formed was collected by filtration and washed with water, isopropanol and ether. Recrystallization from isopropanol gave bis(4,4'-methylthio)benzoin, m.p. 131°–134°.

Bis(4,4'-methylthio)benzoin (10 g, 0.033 mol) was covered with 25 ml of thionyl chloride under a nitrogen atmosphere. After gas evolution ceased, the mixture was refluxed for five minutes. The mixture was then cooled and the volatile components were evaporated. Petroleum ether was added to the residue, the mixture was again evaporated and the residue was recrystallized from methylene chloride and hexane to give 2-chloro-1,2-di(4-methylthiophenyl)ethanone, m.p. 119°–120°.

To 9.0 g (0.028 mol) of 2-chloro-1,2-di(4-methylthiophenyl)ethanone in 50 ml of dry N,N-dimethylformamide was added 7.0 g (0.084 mol) of 2-amino-4,5-dihydro-3H-pyrrole. The mixture was stirred for 48 hours at ambient temperature, then poured into 1 liter of ice containing 300 ml of 5% aqueous sodium carbonate solution. The precipitate was collected by filtration and dissolved in methylene chloride. The solution was washed with water, dried ($K_2CO_3$) and evaporated to give a residue which was chromatographed on alumina and eluted with methylene chloride-methanol (95:5) to give the title compound, m.p. 127°–128°.

$C_{20}H_{20}N_2S_2$:
Calculated: 68.14% C; 5.72% H; 7.95% N; Found: 67.76% C; 5.76% H; 7.91% N.

EXAMPLE 6

| Ingredients | Amounts |
|---|---|
| 2,3-di(4-methylthiophenyl)-6,7-dihydro-5H-pyrrolo[1,2-a]imidazole | 50 mg. |
| magnesium stearate | 5 mg. |
| lactose | 100 mg. |

The above ingredients are screened, mixed and filled into a hard gelatin capsule.

EXAMPLE 7

| Ingredients | Amounts |
|---|---|
| 2,3-di(4-methylthiophenyl)-6,7-dihydro-5H-pyrrolo[1,2-a]imidazole | 100 mg. |
| calcium sulfate dihydrate | 150 mg. |
| sucrose | 20 mg. |
| starch | 10 mg. |
| talc | 5 mg. |
| stearic acid | 3 mg. |

The sucrose, calcium sulfate dihydrate and 2,3-di(4-methylthiophenyl)-6,7-dihydro-5H-pyrrolo[1,2-a]imidazole are mixed and granulated with 10% gelatin solution. The wet granules are screened, dried, mixed with the starch, talc and stearic acid, screened and compressed into a tablet.

EXAMPLE 8

| Ingredients | Amounts |
|---|---|
| 2,3-di(4-methylthiophenyl)-6,7-dihydro-5H-pyrrolo[1,2-a]imidazole | 50 mg. |
| magnesium stearate | 5 mg. |
| lactose | 75 mg. |

The above ingredients are screened, mixed and filled into a hard gelatin capsule.

Similarly, the other compounds of Formula I may be formulated into pharmaceutical compositions by the procedures of Examples 6–8.

These pharmaceutical compositions are adminstered orally to a subject in need of regulation of cell-mediated immunity and/or antiarthritic activity within the dose ranges given hereabove.

What is claimed is:

1. A compound of the formula:

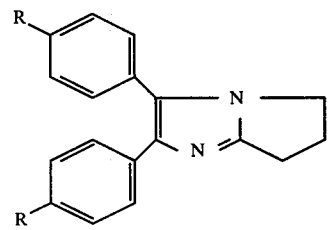

in which:
R is lower alkoxy of from one to four carbon atoms, methylthio or chloro, or a non-toxic pharmaceutically acceptable salt thereof.

2. A compound as claimed in claim 1 where R is methoxy.

3. A compound as claimed in claim 1 where R is ethoxy.

4. A compound as claimed in claim 1 where R is isopropoxy.

5. A compound as claimed in claim 1 where R is methylthio.

6. A compound as claimed in claim 1 wherein R is chloro.

7. A pharmaceutical composition for the regulation of cell-mediated immunity, in dosage unit form, comprising a pharmaceutical carrier and a compound of claim 1 where R is isopropoxy, methylthio or chloro.

8. A pharmaceutical composition having antiarthritic activity, in dosage unit form, comprising a pharmaceutical carrier and a compound of claim 1 where R is methoxy, ethoxy, methylthio or chloro.

9. A pharmaceutical composition for the regulation of cell-mediated immunity and having antiarthritic activity, in dosage unit form, comprising a pharmaceutical carrier and a compound of claim 1 where R is methylthio or chloro.

10. A method of regulating cell-mediated immunity which comprises administering internally to an animal in need thereof an effective amount of a compound of claim 1 where R is isopropoxy, methylthio or chloro.

11. A method of producing antiarthritic activity which comprises administering internally to an animal in need thereof an effective amount of a compound of claim 1 where R is methoxy, ethoxy, methylthio or chloro.

12. A method of regulating cell-mediated immunity and producing antiarthritic activity which comprises administering internally to an animal in need thereof an effective amount of a compound of claim 1 where R is methylthio or chloro.

* * * * *